United States Patent [19]

Goldenberg

[11] Patent Number: 5,659,128
[45] Date of Patent: Aug. 19, 1997

[54] FLUID AGING MONITORING DEVICE

[75] Inventor: Emanuel Goldenberg, Poissy, France

[73] Assignee: Institut Francais du Petrole, Rueil Malmaison, France

[21] Appl. No.: 481,256

[22] PCT Filed: Oct. 27, 1994

[86] PCT No.: PCT/FR94/01253

§ 371 Date: Apr. 15, 1996

§ 102(e) Date: Apr. 15, 1996

[87] PCT Pub. No.: WO95/12119

PCT Pub. Date: May 4, 1995

[30] Foreign Application Priority Data

Oct. 29, 1993 [FR] France .................. 93 13041

[51] Int. Cl.[6] ........................................ G01N 17/00
[52] U.S. Cl. ................................. 73/53.01; 73/86
[58] Field of Search .............. 73/86, 53.01, 61.41, 73/61.42, 61.61; 422/53, 119

[56] References Cited

U.S. PATENT DOCUMENTS

| | | | |
|---|---|---|---|
| 3,253,219 | 5/1966 | Littler | 73/86 |
| 4,306,127 | 12/1981 | Payne | 200/61.04 |
| 5,181,536 | 1/1993 | Argyle et al. | 73/86 X |
| 5,253,674 | 10/1993 | Argyle et al. | 73/86 X |
| 5,373,728 | 12/1994 | Guentzler | 73/86 X |

FOREIGN PATENT DOCUMENTS

| | | | |
|---|---|---|---|
| 808918 | 2/1981 | U.S.S.R. | 73/86 |
| 16614 | 10/1991 | WIPO | 73/86 |
| 17423 | 11/1991 | WIPO | 73/86 |

*Primary Examiner*—Hezron E. Williams
*Assistant Examiner*—Daniel S. Larkin
*Attorney, Agent, or Firm*—Antonelli, Terry, Stout & Kraus, LLP.

[57] ABSTRACT

The present invention relates to a device for monitoring the aging of coolants circulating in heat exchange circuits. It includes an element (4) in contact with said liquid to be monitored, an electric element (51) separated from element (4) in contact with the liquid by an insulating volume (6) containing a fluid at a given pressure, said electric element reacting to the corrosion level of the element in contact, and an alarm (8) reacting to a signal variation of the electric element. According to the invention:

the element in contact with the liquid to be monitored consists of at least one pellet (41) made from a material also present in the circuit and in contact with said fluid (3) in the circuit, and the electric element consists of an element made from a piezoelectric material whose frequency varies with a pressure variation in the insulating volume (6).

5 Claims, 1 Drawing Sheet

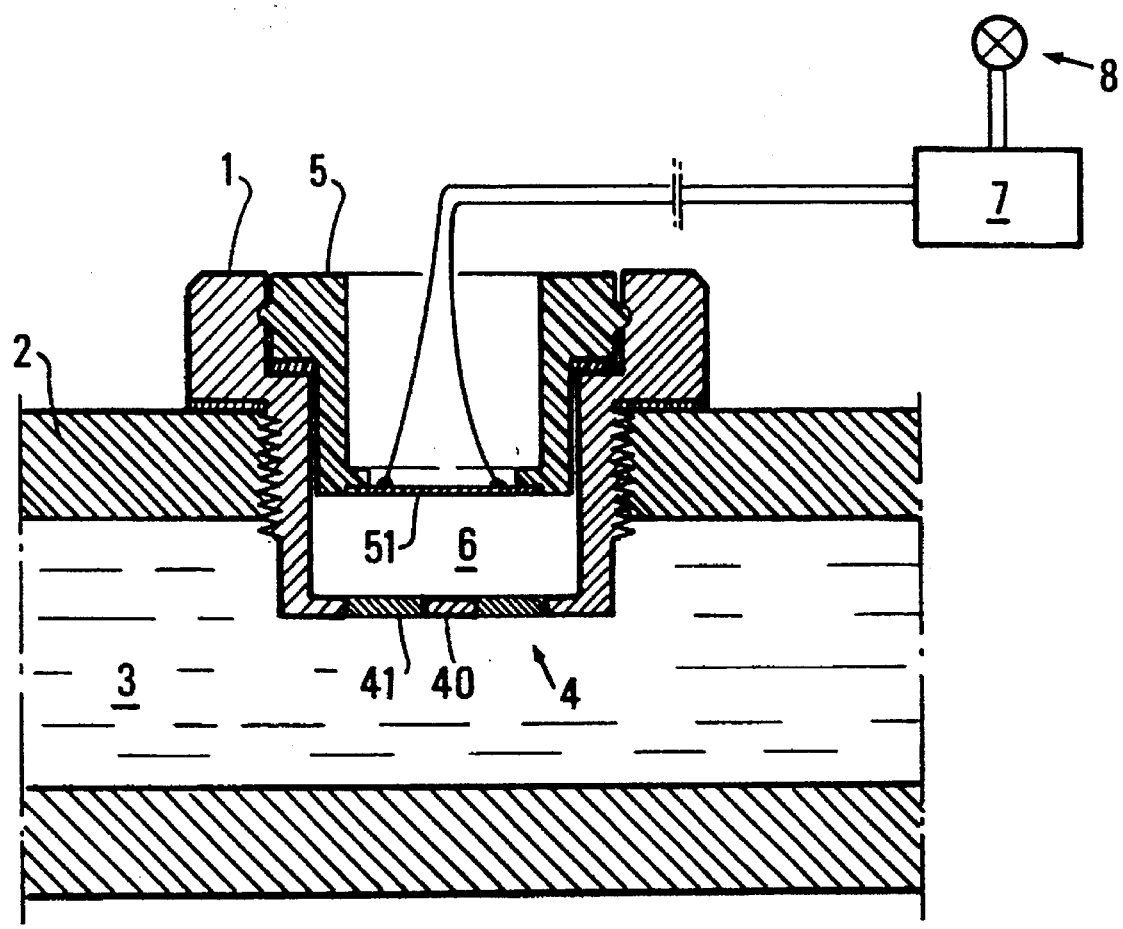

FLUID AGING MONITORING DEVICE

FIELD OF THE INVENTION

The present invention relates to the field of in-situ monitoring of coolants circulating in heat exchangers, and more particularly to the monitoring of their corrosion level.

The present invention is preferably used to control at what time the coolant circulating in internal-combustion engines becomes corrosive.

BACKGROUND OF THE INVENTION

It is well-known that, in an internal-combustion engine, the coolant, apart from its heat exchange function, also allows the engine cooling circuit to be protected from the main degradation forms which it is subjected to. Pitting corrosion, metal tearing by cavitation, electrochemical corrosion, . . . , are the most frequent degradation forms, which are likely to cause great disturbances or even engine damage if they are not detected in time.

In order to fulfill this protective function, coolants thus require a specifically designed formulation. They contain additives for protecting the various metals of the cooling circuit.

However, during operation, the formulation of the coolant may vary by decay or impoverishment of certain additives This modification poses problems because the coolant may thus damage certain materials of the circuit.

It is currently necessary to change periodically and arbitrarily the coolant in order to avoid circuit attacks such as those described above.

Among the known detection and monitoring systems of connected application, document U.S. Pat. No. 4,792,791 discloses a device for monitoring the quality of the lubricating oil of an engine through the corrosion of a resistant element which is part of an electric circuit.

When the resistant element is corroded by the oil in which it is immersed, its resistance varies, then this variation is recorded and considered as a sign of aging of the oil.

Exploitation of the resistance variation of a corrodible sensitive element is also disclosed in documents U.S. Pat. No. 4,675,662, U.S. Pat. No. 4,782,332 or in patent application FR-2,689,240 filed by the applicant.

Although such systems give satisfaction since they allow the aging of an oil or of another engine operating liquid to be monitored, they react only when the degradation or the aging of the oil is in a rather advanced state.

This type of detectors is not sensitive enough to detect for example corrosion of a small zone of the circuit, which would cause no resistance variation. In fact, most of them signal an anomaly only from a certain degradation level.

Besides, if the circuit is made from differents materials, it is not certain that the detector is sensitive enough to all the materials.

SUMMARY OF THE INVENTION

The present invention allows these drawbacks to be remedied by proposing a device for monitoring the aging of coolants circulating in heat exchangers, including a sensor element in contact with said liquid, an electric element separated from the sensor element in contact with the liquid by an insulating volume containing a fluid at the atmospheric pressure, said electric element reacting to the corrosion level of the sensor element in contact, and an alarm reacting to a signal variation of the electric element.

According to the invention:
the sensor element in contact with the liquid to be monitored consists of at least one pellet made from a material also in contact with said liquid in the circuit,
the electric element consists of an element made from a piezoelectric material whose frequency varies with a pressure variation in the insulating volume.

The thickness of each pellet is advantageously such that said pellet is perforated or broken under the joint effect of its own corrosion and of the pressure difference between the pressure P2 which the fluid (3) to be monitored is subjected to and the pressure P1 in the insulating volume (6), the breaking of the pellet occurring before the corresponding part of the circuit is noticeably corroded itself.

More precisely, the device according to the invention may include several pellets of different nature, each one being made from a material also in contact with the liquid in the circuit.

The device according to the invention is preferably located in a place of the circuit where the circulation rate of the fluid is the highest.

According to a particular application, the device according to the invention is used in an internal-combustion engine.

More specifically, the present invention may be used for monitoring the aging of the coolant circulating in internal-combustion engines.

BRIEF DESCRIPTION OF THE DRAWING

Other features and advantages of the invention will be clear from reading the description hereafter, given by way of non limitative examples, with reference to the accompanying sole figure.

DESCRIPTION OF THE PREFERRED EMBODIMENTS

According to this figure, the detector includes a body 1 which may be fastened by any means known in the art to a pipe 2 in which the liquid to be monitored circulates. Fastening may be achieved by nesting and locking or by screwing. A pressure P2 prevails inside pipe 2.

The detector according to the invention is preferably located in a place of the circuit where the circulation rate of the fluid is the highest, or where the fluid moves in a different direction, in order to have a maximum contact with the liquid 3 to be monitored and to amplify the cavitation effect.

The body 1 of the detector may for example be cylindrical, with at least one first bottom 4 in contact with the liquid 3 to be monitored. The first bottom 4 may be closed by a sealed disk 40 to which several sensitive membranes (or pellets) 41 whose characteristics are described hereafter are preferably fastened.

Without departing from the scope of the invention, pellets 41 may be fastened directly to bottom 4.

The other end of body 1, which is not in contact with liquid 3, is closed by a deformable second bottom 5 fastened to body 1 so as to form a sealed volume 6 inside body 1. A pressure P1 such as for example the atmospheric pressure prevails inside volume 6.

A piezoelectric element 51 which is part of an electric circuit 7 is fastened to the second bottom 5, said circuit, whose source may be for example the battery of the engine, further including an alarm means 8 reacting to any frequency variation of the piezoelectric element.

The sensitive pellet or pellets are corrodible, each one being of a different nature. Each of the materials in contact with the liquid to be monitored may advantageously form the material of a pellet. Of course, a single pellet 41 is enough of one wishes to monitor only the corrosion of a single material or if the whole of the circuit is made from a single material.

The thickness of each pellet, which is only a fraction of the thickness of the equivalent material in the circuit, is calibrated by taking account notably of the thickness of the equivalent material in the circuit, of the physico-chemical properties of this material (notably its corrosion rate), and of the pressure difference between pressure P2 in pipe 2 and pressure P1 in volume 6 inside the detector, pressure P2 being normally higher than pressure P1 in the sealed and insulating volume 6.

The detector according to the invention works as follows:

When one of the sensitive pellets 41 is corroded to the point where the liquid to be monitored tears or perforates said pellet, said liquid 3 suddenly fills up inner volume 6 and comes into contact with piezoelectric element 51, which causes a change in the oscillation frequency thereof.

This change is immediately detected at the level of electric circuit 7 and causes the setting on of alarm 8.

Of course, alarm 8 may have any form suited to the wanted application: warning light, sound signal, . . .

The sensitive pellet or pellets 41 are of course so designed that they tear long before the corresponding material of the circuit meets with the same fate. The breaking of the sensitive pellets preferably takes place from the beginning of the appearance of the phenomenon to be monitored, i.e. long before the circuit is damaged.

Fastening of the pellets 41 to bottom 4 may be obtained by sticking or by crimping, with or without an insulating joint.

In the latter case, a corrosion due to electrochemical interactions between the various materials making up the detector adds further to the corrosion phenomenon due to the aging of the coolant. This may be interesting if one wishes to make the pellets even more sensitive to corrosion.

Of course, other modifications or additions may be provided to the device described above by the man skilled in the art without departing from the scope of the present invention.

What is claimed:

1. A detector device for monitoring the aging of a liquid cooling circulating in a heat exchange circuit which comprises a sensor element having a portion in contact with said liquid coolant in the heat exchange circuit, an electric element which is part of an electric circuit and which is separated from the portion of the sensor element in contact with the liquid coolant, a sealed space being defined between the electric element and the portion of the sensor element in contact with the liquid coolant, said space containing a fluid other than a liquid coolant at a given pressure P1, said electric element being sensitive to the corrosion level of a portion of the sensor element in contact with the liquid coolant, and an alarm responsive to a signal variation generated by the electric element; the portion of the sensor element in contact with the liquid coolant to be monitored comprising at least one pellet made of a material which is corrodible upon aging of said liquid coolant and the electric element comprising an element made of the piezoelectric material having a frequency that varies with pressure variation in said sealed space; the thickness of the at least one pellet being such that the pellet is perforated or broken under the joint effect of corrosion by aged liquid coolant and of a pressure difference between a pressure P2 to which the liquid coolant to be monitored is subjected to in the circuit and the pressure P1 in the sealed space, the breaking of the at least one pellet occurring before a corresponding part of a material forming the heat exchange circuit is noticeably corroded.

2. A device according to claim 1, wherein said portion of the sensor element in contact with the liquid coolant extends into a pipe forming part of the heat exchange circuit and said portion of the sensor element includes several pellets of different material each pellet being corrodible by the aging of the liquid coolant and each of said different materials corresponding to a different material forming in the heat exchange circuit.

3. A device according to claim 1, wherein the sensor element is positioned in that part of heat exchange circuit where a circulation rate of the liquid coolant is the highest.

4. A device according to claim 1 in combination with a cooling system of an internal-combustion engine.

5. A device according to claim 4, wherein the sensor element comprises a tubular body which extends into a pipe through which the liquid coolant flows in the heat exchange circuit and the portion of the sensor element in contact with the liquid coolant comprises a bottom portion spaced from the electric element, said electric element being housed within the sensor element.

* * * * *